United States Patent [19]

Leonard et al.

[11] Patent Number: 4,962,319

[45] Date of Patent: Oct. 9, 1990

[54] REMOTE SUBSURFACE WATER TEMPERATURE MEASURING APPARATUS WITH BRILLOUIN SCATTERING

[75] Inventors: Donald A. Leonard, Cupertino; Harold E. Sweeney, Menlo Park, both of Calif.

[73] Assignee: GTE Government Systems Corporation, Stamford, Conn.

[21] Appl. No.: 400,217

[22] Filed: Aug. 29, 1989

Related U.S. Application Data

[63] Continuation-in-part of Ser. No. 386,383, Jul. 28, 1989.

[51] Int. Cl.$^5$ .................. G01N 15/06; G01J 5/00; G01B 9/02
[52] U.S. Cl. .................. 250/574; 250/231.1; 374/121; 374/127; 374/137; 356/349; 356/43
[58] Field of Search .................. 250/574, 231 R; 374/120, 121, 117, 124, 127, 136, 137; 356/43, 301, 318, 342, 349

[56] References Cited

U.S. PATENT DOCUMENTS

| | | | |
|---|---|---|---|
| 4,057,349 | 11/1977 | Barrett | 356/301 |
| 4,123,160 | 10/1978 | Caputo et al. | 356/43 |
| 4,411,525 | 10/1983 | Ogawa | 356/339 |
| 4,637,716 | 1/1987 | Auweter et al. | 356/349 |
| 4,767,219 | 8/1988 | Bibby | 356/301 |
| 4,823,166 | 4/1989 | Hartog et al. | 356/44 |
| 4,859,065 | 8/1989 | Bibby | 356/44 |
| 4,867,558 | 9/1989 | Leonard et al. | 356/43 |
| 4,867,564 | 9/1989 | Sweeney et al. | 356/349 |

OTHER PUBLICATIONS

Hirschberg et al., "Speed of Sound and Temperature in the Ocean by Brillouin Scattering", *Applied Optics*, vol. 23, No. 15, 8/84, pp. 2624–2628.

*Primary Examiner*—David C. Nelms
*Assistant Examiner*—Michael Messinger
*Attorney, Agent, or Firm*—Douglas M. Gilbert; John F. Lawler

[57] ABSTRACT

Apparatus is disclosed for remotely sensing the unknown subsurface temperature $T_s$ of a bulk transparent medium, such as ocean water, using a cw laser beam and a pulsed laser beam. In one embodiment the cw output of a continuous laser is split into two sub-beams. An optical amplifier periodically amplifies the first such sub-beam thereby generating an intense pulsed laser beam having a plurality of pulses with the same wavelength as the cw laser beam. The intensity level of the pulses is sufficient to produce stimulated Brillouin scattering when focussed into the ocean water. The pulsed laser beam is directed into the water thereby generating an intense return phase-conjugate beam propagating along the path of the pulsed laser beam but in the opposite direction thereto. The phase-conjugate beam and the second sub-beam are mixed at the cathode of a photodetector to produce a heterodyne frequency proportional to the temperature $T_s$. A frequency measuring instrument converts the heterodyne frequency into a temperature value equal to $T_s$. Since the cw beam in always present at the photodetector for mixing with the return phase-conjugate pulses, the path lengths of the cw laser beam and the pulsed laser beam may be unequal.

9 Claims, 3 Drawing Sheets

5°C

20°C

10°C

25°C

15°C

30°C

REMOTE SUBSURFACE WATER TEMPERATURE MEASURING APPARATUS WITH BRILLOUIN SCATTERING

This invention was made with Government support under Contract No. N00014-87-C-0739 awarded by the Department of the Navy. The Government has certain rights in this invention.

RELATED APPLICATION

This application is a Continuation-in-part of co-pending patent application Ser. No. 386,383, filed July 28, 1989.

The invention described herein also relates generally to the following patent applications:

"Apparatus for and Method of Remotely Sensing Sub-Surface Water Temperatures," Ser. No. 64,371, filed June 27, 1987 now U.S. Pat. No. 4,867,564.

"Method of Remotely Detecting Submarines Using a Laser," Ser. No. 64,375, filed June 22, 1987 now U.S. Pat. No. 4,867,558.

"Remote Subsurface Water Temperature Measuring Apparatus," Ser. No. 387,735, filed Aug. 1, 1989, "A Remote Method of Measuring Subsurface Water Temperatures," Ser. No. 386,383, filed July 28, 1989.

BACKGROUND OF THE INVENTION

1. Field of the Invention

This invention relates to the remote measurement of the properties of transparent media, such as subsurface ocean temperatures profiles, and in particular to apparatus for remotely measuring such temperature profiles from surface or subsurface vessels or aircraft.

2. Description of the Prior Art

There are several applications for remotely sensing or measuring the temperature of a bulk transparent medium such as water. One such applications is the sounding of temperature profiles in the ocean which is useful for a variety of oceanographic purposes such as measuring the depth of the thermocline, sensing internal waves, measuring heat content of oceans for meteorological applications and mapping acoustical propagation paths sensitive to temperature gradients. Insitu temperature sensors such as thermistors, thermocouples, etc. have been used in the past for these purposes but, because they are not remote sensors, are slow and awkward. A remote sensing technique in wide use is the monitoring of thermal radiation; this technique, however, is limited to measuring predominantly surface temperatures.

This invention is directed to improved apparatus for remotely measuring temperature within, i.e., below the surface of suitable transparent media or substances, as for example sea water.

OBJECTS AND SUMMARY OF THE INVENTION

A general object of the invention is the provision of apparatus for measuring the subsurface temperature of a transparent substance remotely and substantially instantly.

A further object is the provision of such apparatus that is relatively compact and highly portable.

Another object is the provision of a measurement technique that has a high signal-to-noise ratio and therefore produces highly accurate measurements.

A further object is the provision of such apparatus in which the irradiance of the received return signal from the target substance is relatively high.

These and other objects of the invention are achieved with apparatus for remotely sensing the unknown subsurface temperature $T_s$ of a bulk transparent medium, such as ocean water, using a continuous-wave (cw) laser beam and a pulsed laser beam. In one embodiment the cw output of a continuous laser is split into first and second sub-beams. An optical amplifier periodically amplifies the first sub-beam thereby generating an intense pulsed laser beam consisting of a plurality of pulses having the same wavelength as the cw laser beam. The intensity level of the pulses is sufficient to produce stimulated Brillouin scattering (SBS) when focused into the medium under test thereby generating a return phase-conjugate beam propagating along the same path as the pulsed beam but in the opposite direction thereto. A partially transmitting mirror separates a portion of the return phase-conjugate beam from the pulsed beam for optical mixing in a photodetector with the second sub-beam. The photodetector heterodynes the two optical signals to derive a difference frequency proportional to the unknown temperature of the medium. And, a frequency converter translates the difference frequency to a value corresponding to the unknown temperature.

BRIEF DESCRIPTION OF THE DRAWINGS

For a better understanding of the invention as well as other objects and further features thereof, reference is made to the following description which is to be read in conjunction with the accompanying drawings wherein.

DESCRIPTION OF PREFERRED EMBODIMENT

Figure 1:
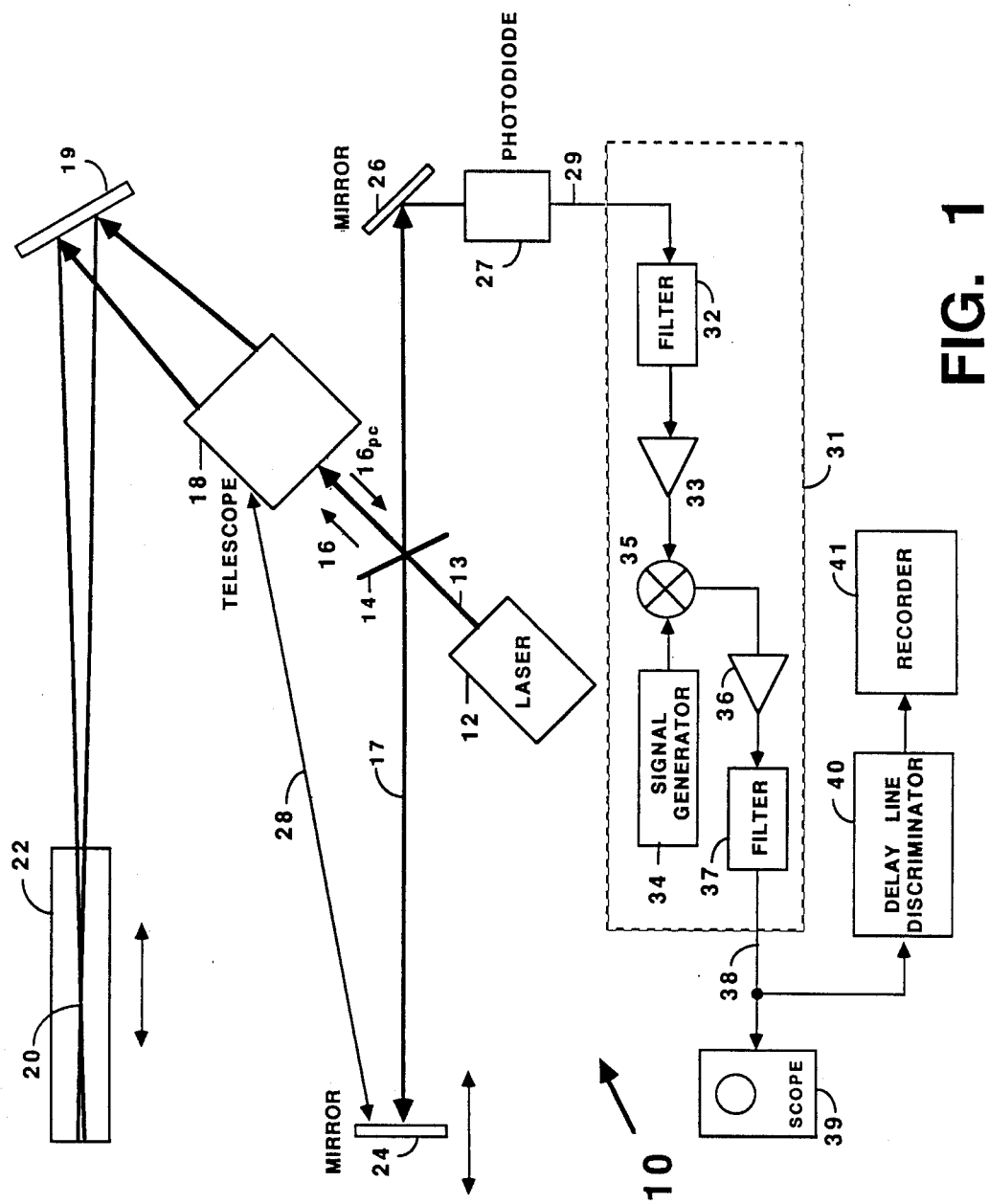
FIG. 1 is a schematic drawing of apparatus for optically measuring temperature in accordance with the invention.
Figure 2A:
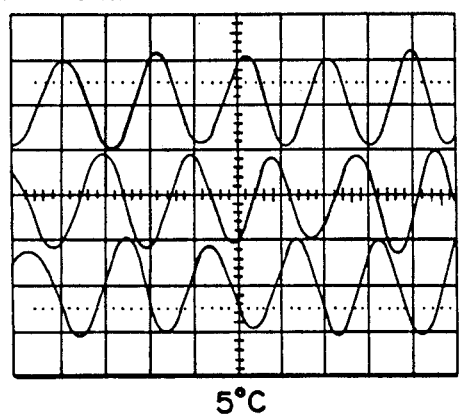
FIG. 2A through 2F are representations of several actual heterodyne waveforms as a function of water temperature at 5° C. intervals as derived from the apparatus depicted in FIG. 1.
Figure 2D:
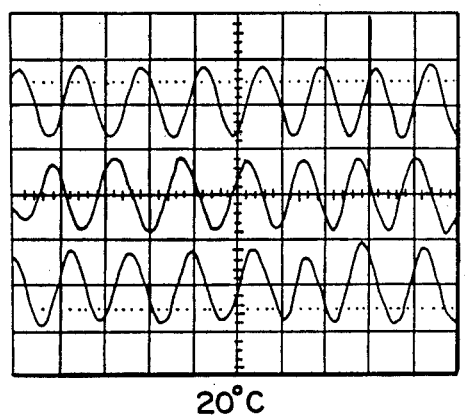
Figure 2B:
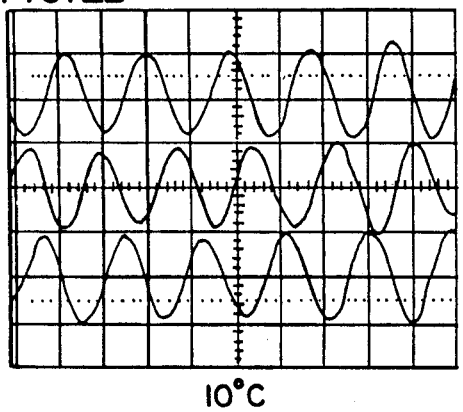
Figure 2E:
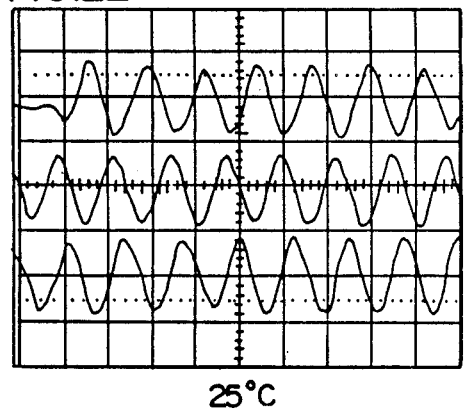
Figure 2C:
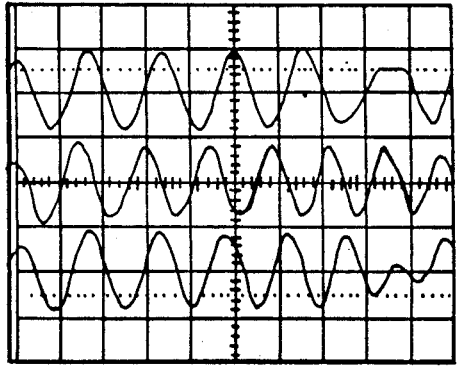
Figure 2F:
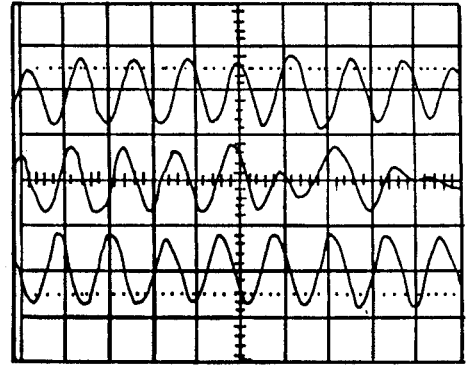

Referring now to the drawings, FIG. 1 illustrates temperature measuring apparatus 10 in which a pulsed laser 12 generates an intense output beam 13. Beam 13 is incident on and split by a beam splitter 14 into a first sub-beam 16 which passes through splitter 14 and a second sub-beam 17 which is reflected thereby. Sub-beam 16 passes through a lens or telescope 18 to a mirror 19 and is focused thereby to a focal point 20 in a transparent medium 22 such as water. Telescope 18 is adjustable so as to enable adjustment of the location of focal point 20 to various selected locations or depths within medium 22 as suggested by the proximate double-headed arrow. The unknown temperature of interest, designated $T_s$, is the temperature of medium 22 at focal point 20.

Sub-beam 17 propagates from splitter 14 to and is reflected by a mirror 24 along the same path back to splitter 14. The spacing of mirror 24 from splitter 14 is variable as indicated by the adjacent double-headed arrow.

The intensity of the pulsed output beam 13, i.e., the intensity or irradiance of the pulses from laser 12 exceeds a predetermined threshold level at which sub-beam 16 produces stimulated Brillouin scattering in cell 22 resulting in the generation of a phase-conjugate or "time-reversed" beam whose ray runs along the same trajectory as but in opposite direction to sub-beam 16. The direction of the pc beam is designated by the arrow $16_{pc}$. This phenomenon, called optical phase conjugation, is well known and is described in detail in articles entitled *Optical Phase Conjugation* by V. V. Shkunov et al, Scientific American, pages 54–59 (September 1985) and *Applications of Optical Phase Conjugation* by D. M. Pepper, Scientific American, pages 74–83 (January 1986).

The Brillouin backscatter optical wave from a spontaneously generated phonon interacts with the probe beam and the interaction produces a traveling electric field that travels exactly at the sound velocity in the particular substance. If the light intensity is great enough and the electrostrictive coefficient of the medium is sufficiently strong, this traveling electric field will create an acoustic field which aligns itself in a column with the probe beam and the backscattered beam at the expense of scattering in other directions. Hence the collection of light is more efficient in the SBS case.

The presence of the induced electric field traveling at the sound velocity can be derived in the following way. Assume that an electromagnetic wave (the probe laser) propagates in a substance in the $+x$ direction with velocity c, then the electric field may be written as $$E_1 = E_o \sin(\omega_1 t - \omega_1 x/c) \quad (1)$$

where,
$E_o$ = magnitude of the wave,
$\omega$ = frequency, and
t = time parameter, and assume that a wave of different frequency (the Brillouin scattering) propagates in the -x direction, the electric field of which is written as, $$E_2 = E_o \sin(\omega_2 t + \omega_2 x/c), \quad (2)$$

where, $\omega_2$ = frequency of the second wave. The total electric field in their common region is $$E = E_1 + E_2 = E_o[\sin(\omega_1 t - \omega_1 x/c) + \sin(\omega_2 t + \omega_2 x/c)] \quad (3)$$

which can be arranged by trigonometric identities to the form $$E = 2E_o\{\sin \tfrac{1}{2}[(\omega_1 + \omega_2)t - (\omega_1 - \omega_2)x/c]\}\{\cos \tfrac{1}{2}[(\omega_1 - \omega_2)t - (\omega_1 + \omega_2)x/c]\} \quad (4)$$

which is of the form of a high frequency ($\omega_1 + \omega_2$) signal modulated with a low frequency ($\omega_1 - \omega_2$) envelope. The velocity of the envelope is found by making its argument constant, i.e., $$(\omega_1 - \omega_2)t - (\omega_1 \omega_2)x/c = K. \quad (5)$$

The envelope velocity is therefore $$\begin{aligned} dx/dt &= (\omega_1 - \omega_2)c/(\omega_1 + \omega_2) \\ &= (f_1 - f_2)c/(f_1 + f_2). \end{aligned} \quad (6)$$

In the case of Brillouin scattering $f_2$ has been produced by Doppler shift by interacting with an acoustic wave at velocity v. The Doppler equation, namely ps $$f_2 = f_1(c-v)/(c+v),$$

which when solved results in the following expression:

$$c = (f_1 + f_2)v/(f_1 - f_2).$$

A substitution into the prior expression (6) for dx/dt yields dx/dt = v. The envelope of the composite electric field wave therefore travels exactly at the acoustic velocity.

In order to achieve SBS, a predetermined threshold intensity level for the optical probe beam must be exceeded. This intensity level must be sufficient so that the following relationship exists:

$$\exp[GIL] \geq 10^{13}$$

or, $$\exp[GIL] \geq \exp[30].$$

(since $10^{13} = \exp[30]$).

Or more simply, the intensity, $I \geq 30/GL$, where,
G = a gain parameter which is a property of the medium, m/W
I = intensity of the optical probe beam (W/m$^2$) and,
L = interaction length, m,
see *Principles of Phase Conjugation* by Zel'dovich et al., Springer-Verlag, Vol. 42, page 29, Springer Series on Optical Sciences (Springer Verlag Berlin Heidelberg, 1985). (For water G is typically $5 \times 10^{-11}$ m/W.)

The sound velocity in water is related to the temperature and salinity and is given in the article entitled *Development of Simple Equations for Accurate and More realistic Calculation of the Speed of Sound in Sea Water* by C. C. Leroy, Journal of Acoustical Society of America, No. 216, page 216 (1969):

$$v = 1492.9 + 3(T-10) - 0.006(T-10)^2 - 0.04(T-18)^2 + 1.2(S-35) - 0.01(T-18)(S-35) + Z/61 \quad (9)$$

where,
T = temperature in degrees C.,
S = salinity in parts per thousand.
Z = depth in meters.

The phase conjugate of sub-beam 16, designate $16_{pc}$, propagates from medium 22 precisely along the path of sub-beam 16 except in the opposite direction to mirror 19 and is reflected thereby through lens 18 to splitter 14 from which it is reflected to mirror 26 and ultimately to photodetector 27, such as a photodiode. Sub-beam 17 reflected from mirror 24 passes through splitter 14 to mirror 26 and is reflected thereby to photodetector 27. It is important that the pulses comprising sub-beam 17 and the pulses comprising pc beam $16_{pc}$ arrive at the active mixing surface photodetector 27 at the same time for effective heterodyning of these two signals. Since there is no optical storage mechanism, if the pulses from the two beams are not properly timed to arrive at the photodetector at substantially the same instant, the two pulses will not mix with each other. To this end, the optical spacing of both focal point 20 and mirror 24 from photodetector 27 are the same. The adjustable spacing between mirror 24 and splitter 14 accommodates this requirement. The adjustment of the location of focal point 20 in medium 22 may also be directly related to adjustment of the position of mirror 24 by means of a mechanical, electromechanical or other suitable link or connection between lens 18 and mirror 24 as indicated by the line 28 between these components.

A phase-conjugated beam derived from SBS has its optical frequency shifted by a frequency that produces an acoustical wavelength in the water equal to half the optical wavelength, i.e.

$$\Delta \nu = (2) \frac{v_a n}{\lambda} \tag{10}$$

where, $\Delta \nu$ = the optical frequency shift,
$v_a$ = the acoustic velocity in water,
$n$ = the index of refraction in water, and
$\lambda$ = the wavelength of the incident beam in a vacuum.

Photodetector 27 mixes sub-beam 17 and beam $16_{pc}$ and produces at its output 29 a difference frequency, $\delta f$, that is proportional to the temperature $T_s$. This frequency may be as high as 8 GHz. In order to enable conversion of a $\delta f$ of this magnitude to an analog temperature value with conventional oscilloscope/recorder equipment, it is desirable to further mix photodetector output 29 to down convert the latter to a lower more manageable frequency. This is accomplished with down converter equipment enclosed within broken lines 31 and comprising a filter 32, an amplifier 33, a signal generator 34, a mixer 35, an amplifier 36 and a filter 37. High-pass filter 32 rejects the basic pulse components in output 29 but preserves the SHF (super high frequency) signal. Amplifier 33 increases the signal level into double-balanced mixer 35 driven by signal generator 34. In fresh water the SHF signal is typically 7.1 to 7.5 GHz; setting the signal generator to 6550 MHz produces an IF (intermediate frequency) between 550 and 950 MHz for convenient viewing on a real time oscilloscope (39) such as Tektronix Model No. 7104. The output 38 of filter 37 is observed by scope 39, and is converted to a voltage by a wide band delay line discriminator 40 which feeds a chart recorder 41. Delay line discriminator 40 is designed to operate between 500 to 1000 MHz.

FIG. 2 shows a series of photographs of the display screen from oscilloscope 39 depicting the heterodyne waveform as a function of medium (water) temperature from 5° to 30° C. at 5 degree intervals. The change in frequency is clearly seen in these photographs at a high signal-to-noise ratio.

Figure 3:
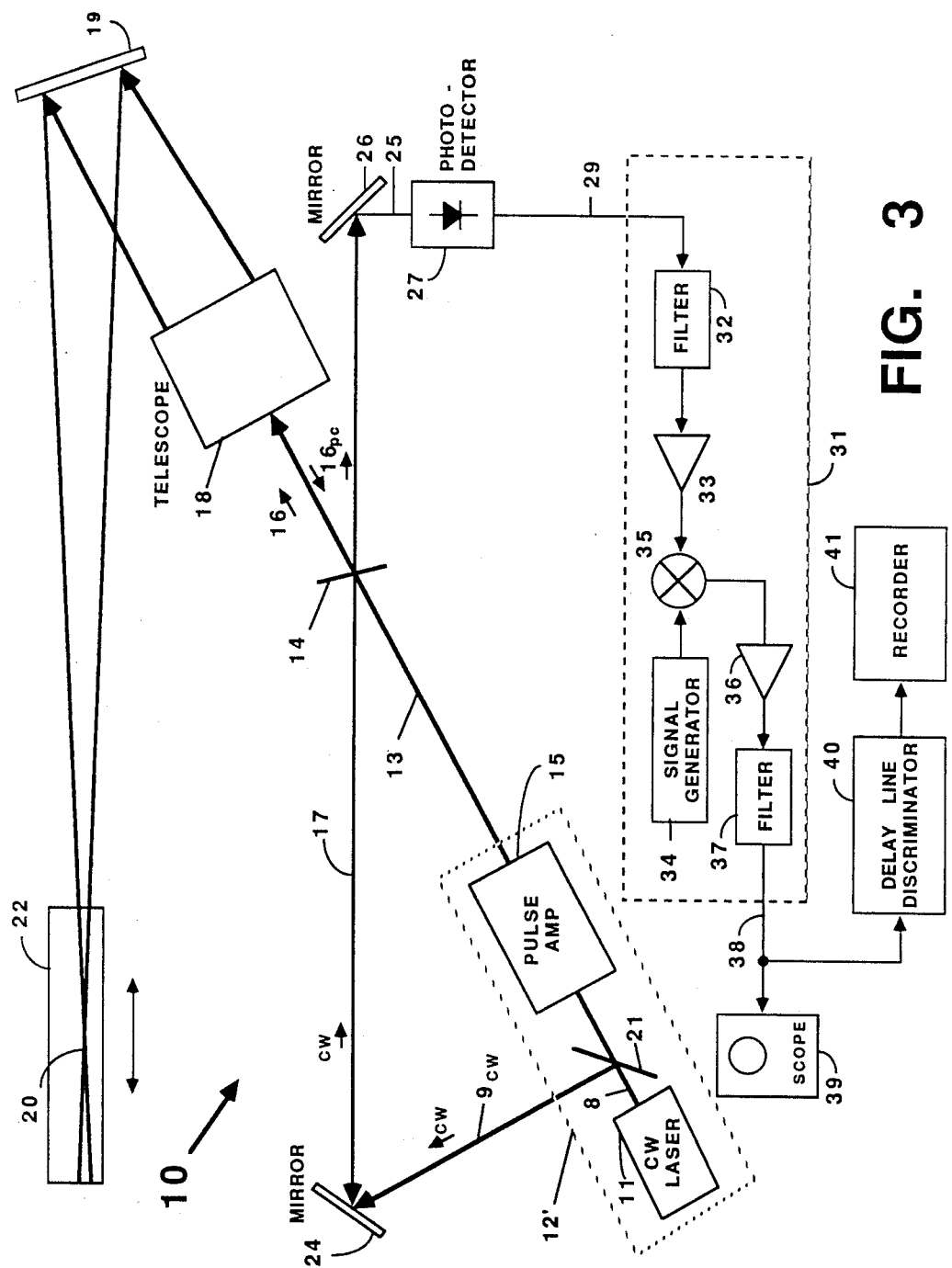
FIG. 3 is a schematic diagram illustrating an alternate embodiment of apparatus used in the practice of the subject invention.

Referring again to FIG. 1, it is important that the pulses comprising sub-beam 17 and the pulses comprising pc beam $16_{pc}$ arrive at the active mixing surface of photodetector 27 at the same time, since there is no optical storage mechanism. This constraint would not exist if one of the beams was continuously present at photodetector 27. Thus, an alternate approach to this temperature measurement technique that solves the pulse timing requirement is to use a continuous-wave reference beam as is shown by the apparatus of FIG. 3. The pulse laser function (laser 12 in FIG. 1) has been replaced with apparatus 12', namely, a cw "seeder" laser (laser 11), beam splitter 21, and pulse laser amplifier 15. Note that the pulse output beam on path 13, which is directed into transparent medium 22, is the same basic signal in both FIG. 1 and FIG. 3. Replacing the pulse laser 12 of FIG. 1 with the cw laser and pulse laser amplifier allows the cw sub-beam $9_{cw}$ on path 17 to be mixed with the return pc beam $16_{pc}$. More precisely, the cw laser beam on path 8 is divided by beam splitter 21, and mirror 24 directs the cw sub-beam (indicated by the cw arrows on path 17) to splitter 14 which combines the CH sub-beam with the SBS beam $16_{pc}$ from medium 22. Since a portion of the CH sub-beam 8 drives pulse amplifier 15, the cw reference beam on path $9_{cw}$ has the same frequency as the pulse beam used to probe the water at point 20. And since the cw portion of the combining signals on path 25 is always present, there is no need to adjust path lengths to maintain time coincidence of the pulses at photodetector 27. Such an arrangement would have particular utility in a situation where maintaining the path lengths to be the same would be difficult, such as in an airplane probing subsurface temperatures with pulse laser beam 16.

While the invention has been described with reference to its preferred embodiment, it will be understood by those skilled in the art that various changes may be made and equivalents may be substituted for the elements thereof without departing from the true spirit and scope of the invention. In addition, many modifications may be made to adapt a particular situation or material to the teaching of the invention without departing from its essential teaching.

What is claimed is:

1. Apparatus for remotely measuring the unknown temperature $T_s$ of a transparent medium, comprising:

first laser means generating a continuous laser beam having a $\lambda_1$ wavelength;

second laser means generating a pulsed laser beam having a $\lambda_1$ wavelength and having an irradiance such that $I \geq 30/GL$ where, G is a gain parameter of said transparent medium (m/W), I is the intensity of said pulsed laser beam, (W/m²), and L is the interaction length (m), means for directing said pulsed laser beam into said medium to produce stimulated Brillouin scattering and thereby causing a phase-conjugate (pc) beam to emanate therefrom;

a photodetector for receiving said continuous laser beam;

means for directing said phase-conjugate beam to said photodetector for mixing with said continuous laser beam and thereby producing a nonoptical difference frequency proportional to the temperature $T_s$; and means for converting said difference frequency into a temperature value.

2. Apparatus according to claim 1 further comprising:
   means for separating said phase-conjugate beam from said pulsed laser beam.

3. Apparatus according to claim 1 in which said first-named beam directing means comprises an adjustable lens for directing said pulsed laser beam into said medium whereby to vary the depth of the beam focusing point in said medium.

4. Apparatus according to claim 3 in which said medium comprises sea water.

5. Apparatus for remotely measuring an unknown subsurface temperature $T_s$ of a body of water, comprising:

a laser having a continuous (cw) output beam of wavelength $\lambda_1$;

optical splitter means for splitting said cw beam into first and second sub-beams;

optical amplifier means periodically amplifying said first sub-beam to an intensity level needed to produce stimulated Brillouin scattering in said body of water, said optical amplifier means generating a pulsed laser beam having a plurality of pulses of wavelength $\lambda_1$;

means for directing said pulsed laser beam into said body of water and thereby generating a return phase-conjugate (pc) beam;

means for separating at least a portion of said return pc beam from said pulsed laser beam;

a photodetector for optically mixing said portion of said pc beam and said second sub-beam thereby generating a difference frequency proportional to $T_s$; and frequency discriminator means for converting said difference frequency into a value of $T_s$.

6. Apparatus according to claim 5 wherein said directing means further comprises:

means for adjustably focusing said pulsed laser beam to a plurality of selected points at different locations within said water whereby to measure the medium temperatures at said points.

7. Apparatus according to claim 6 in which said wavelength $\lambda_1$ is in the blue-green spectrum.

8. Apparatus as in claim 6 further comprising:

airborne platform means for housing each of said aforementioned means, said platform means including an optical window for transmitting said pulsed beam and for receiving said return phase-conjugate beam.

9. Apparatus for remotely measuring the subsurface temperatures $T_s$ of sea water comprising:

a laser having a continuous (cw) output beam of wavelength $\lambda_1$;

optical splitter means for splitting said cw beam into first and second sub-beams;

optical amplifier means periodically amplifying said first sub-beam and generating a pulsed laser beam having a plurality of pulses of wavelength $\lambda_1$;

means for directing and focusing said pulsed laser beam into the sea water at a predetermined focal point, said pulsed laser beam having an intensity sufficient to cause stimulated Brillouin scattering in the sea water at said focal point and thereby generating a return phase-conjugate beam of wavelength $\lambda_2$ emanating from the sea water;

means for separating a portion of said return phase-conjugate beam from said pulsed laser beam;

a photodetector sensitive to an optical spectrum including the wavelengths $\lambda_1$ and $\lambda_2$;

means for simultaneously directing said portion of said return phase-conjugate beam and said second sub-beam onto said photodetector;

means for extracting a difference frequency $\delta f$ from said photodetector; and means for converting said $\delta f$ into a value corresponding to the temperature $T_s$.

* * * * *